United States Patent
Seaver et al.

(10) Patent No.: US 9,682,221 B2
(45) Date of Patent: Jun. 20, 2017

(54) TUNNELING GUIDEWIRE

(71) Applicant: Arkis Biosciences Inc., Knoxville, TN (US)

(72) Inventors: Chad Eric Seaver, Knoxville, TN (US); James Chris Arnott, Knoxville, TN (US); James Alexander Killeffer, Knoxville, TN (US)

(73) Assignee: Arkis BioSciences Inc., Knoxville, TN (US)

(*) Notice: Subject to any disclaimer, the term of this patent is extended or adjusted under 35 U.S.C. 154(b) by 0 days.

(21) Appl. No.: 15/237,024

(22) Filed: Aug. 15, 2016

(65) Prior Publication Data

US 2016/0346523 A1    Dec. 1, 2016

Related U.S. Application Data

(62) Division of application No. 14/660,616, filed on Mar. 17, 2015, now Pat. No. 9,427,558.
(Continued)

(51) Int. Cl.
*A61M 21/00* (2006.01)
*A61M 27/00* (2006.01)
(Continued)

(52) U.S. Cl.
CPC ....... *A61M 27/006* (2013.01); *A61B 17/3415* (2013.01); *A61M 25/0194* (2013.01);
(Continued)

(58) Field of Classification Search
CPC ............... A61M 27/006; A61M 25/09; A61M 2025/09116; A61M 2025/09175;
(Continued)

(56) References Cited

U.S. PATENT DOCUMENTS

| 4,149,535 A | 4/1979 | Volder |
| 4,318,401 A | 3/1982 | Zimmerman |

(Continued)

FOREIGN PATENT DOCUMENTS

| DE | 69633411 | 10/2005 |
| WO | 9952481 | 10/1999 |

(Continued)

OTHER PUBLICATIONS

International Search Report and Written Opinion issued in International Application No. PCT/US2015/020979 mailed Jun. 26, 2015.
(Continued)

*Primary Examiner* — Alexander Orkin
(74) *Attorney, Agent, or Firm* — Meunier Carlin & Curfman LLC

(57) ABSTRACT

A medical device tunneling system, and a method of using the same, to subcutaneously route trocars, also commonly referred to as tunnelers, or introducers, having a cannula, stylet, and a guidewire stylet, inside a patient during a surgical procedure, such as a ventriculoperitoneal hydrocephalus shunt implantation, from a proximal entry point to a distal end point, in order to subcutaneously route and implant a medical device, such as shunt tubing, in a patient.

21 Claims, 4 Drawing Sheets

Related U.S. Application Data

(60) Provisional application No. 61/953,985, filed on Mar. 17, 2014.

(51) Int. Cl.
  *A61B 17/34* (2006.01)
  *A61M 25/01* (2006.01)
  *A61M 25/09* (2006.01)

(52) U.S. Cl.
  CPC .............. *A61M 25/09041* (2013.01); *A61M 2025/09125* (2013.01); *A61M 2025/09175* (2013.01)

(58) Field of Classification Search
  CPC ......... A61M 2025/01983; A61M 2025/09133; A61B 17/34
  See application file for complete search history.

(56) References Cited

U.S. PATENT DOCUMENTS

| | | | |
|---|---|---|---|
| 4,464,178 A | 8/1984 | Dalton | |
| 4,475,898 A | 10/1984 | Brodner et al. | |
| 4,631,051 A | 12/1986 | Harris | |
| 4,846,186 A | 7/1989 | Box et al. | |
| 4,950,232 A | 8/1990 | Ruzicka et al. | |
| 5,183,464 A | 2/1993 | Dubrul et al. | |
| 5,356,390 A | 10/1994 | Erskine | |
| 5,370,640 A | 12/1994 | Kolff | |
| 5,385,541 A | 1/1995 | Kirsch et al. | |
| 5,704,352 A | 1/1998 | Tremblay et al. | |
| 5,762,615 A * | 6/1998 | Weier | A61M 25/09 600/585 |
| 5,916,193 A | 6/1999 | Stevens et al. | |
| 5,944,732 A | 8/1999 | Raulerson et al. | |
| 5,980,504 A | 11/1999 | Sharkey et al. | |
| 6,007,510 A | 12/1999 | Nigam | |
| 6,007,544 A | 12/1999 | Kim | |
| 6,197,041 B1 | 3/2001 | Shichman et al. | |
| 6,267,769 B1 | 7/2001 | Truwit | |
| 6,655,386 B1 * | 12/2003 | Makower | A61B 1/3137 128/898 |
| 6,902,547 B2 | 6/2005 | Aves et al. | |
| 7,134,438 B2 | 11/2006 | Makower et al. | |
| 7,189,222 B2 | 3/2007 | Elsberry | |
| 7,678,100 B2 | 3/2010 | Chin et al. | |
| 7,942,826 B1 | 5/2011 | Scholl et al. | |
| 8,177,772 B2 | 5/2012 | Christensen et al. | |
| 8,337,475 B2 | 12/2012 | Christensen et al. | |
| 8,768,487 B2 | 7/2014 | Farman et al. | |
| 8,784,330 B1 | 7/2014 | Scholl et al. | |
| 2002/0121282 A1 | 9/2002 | McGuckin, Jr. et al. | |
| 2005/0171452 A1 | 8/2005 | Neff | |
| 2007/0179426 A1 | 8/2007 | Selden | |
| 2008/0051721 A1 * | 2/2008 | Carter | A61M 25/09 604/164.13 |
| 2008/0161843 A1 | 7/2008 | Clague et al. | |
| 2008/0194993 A1 | 8/2008 | McLaren et al. | |
| 2008/0262406 A1 | 10/2008 | Wiener | |
| 2009/0048537 A1 | 2/2009 | Lydon et al. | |
| 2009/0171367 A1 | 7/2009 | Hardin, Jr. | |
| 2010/0211048 A1 | 8/2010 | Arai et al. | |
| 2010/0222732 A1 | 9/2010 | Sevrain | |
| 2013/0267982 A1 | 10/2013 | Seaver et al. | |

FOREIGN PATENT DOCUMENTS

| | | |
|---|---|---|
| WO | 2007089724 | 8/2007 |
| WO | 2013147978 | 10/2013 |

OTHER PUBLICATIONS

Sandquist, Michael A., A Single-Pass Tunneling Technique for CSF Shunting Procedures, Pediatric Neurosurgery, 2003, 39:254-257.

* cited by examiner

TUNNELING GUIDEWIRE

CROSS-REFERENCE TO RELATED APPLICATIONS

This application is a divisional of U.S. patent application Ser. No. 14/660,616, filed Mar. 17, 2015, which claims priority to U.S. Provisional Patent Application No. 61/953,985, filed Mar. 17, 2014, both of which are hereby incorporated by reference in their entireties.

FIELD OF INVENTION

The present general inventive concept relates generally to a system and method to subcutaneously route a path in a patient to form a continuous path in order to route tubing between two or more biological entry points.

BACKGROUND

Conventionally, in the case of a hydrocephalus surgical shunt installation procedure with the ventricular catheter located approximately at the top of the patient's skull, three incisions are typically required to install the hydrocephalus shunt. FIG. 1 is a schematic illustration of incision locations performed in a traditional hydrocephalus shunt installation procedure. Referring to FIG. 1, the incision locations applied to a patient during a hydrocephalus shunt surgical installation procedure are generally indicated by 100. The box shapes at the incision locations are intended to indicate the general area of the incisions, rather than the shape or size of the incisions. These three incisions, which can be made in any order, are located at the patient's scalp forming a first incision 101, abdomen forming a second incision 102, and at the patient's neck forming a third incision 103. Once the incisions are made the shunt tubing is subcutaneously tunneled from the abdomen incision 102 to the third incision 103, using, for example, a long trocar, which may also be referred to as a tunneler, and/or inserter, and/or introducer and/or cannula, and which may contain a stylet. Then the shunt tubing is further manually subcutaneously tunneled by common surgical hand tools, such as forceps, from the third incision 103 to the first incision 101 forming a complete and continuous subcutaneous path between the first and second incisions. The third incision 103 is generally required because of the extreme curvilinearity of the path between the first and second incisions 101 and 102, and prevents direct tunneling between the first and second incisions with a typical semi-rigid, manipulatable trocar/tunneling instrument for passage overcoming the nuchal line. It is advantageous to minimize the number of incisions required to perform the surgical procedure in order to minimize bodily trauma, the possibility of infection, and recovery time. It is noted that performance of the steps are not necessarily performed in a fixed sequence of steps but as to the most convenient and judgment of the user.

Therefore, there exists a desire for a surgical tool that allows a surgeon to route a shunt drainage tube between the first and second incisions without the necessity of the third incision to both increase surgical productivity and minimize patient trauma.

SUMMARY

A method of subcutaneously routing tubing within a human patient is disclosed herein. The method can include, for example, making a first incision; inserting at least a portion of a stylet into a cannula, wherein the cannula comprises a hollow passage; inserting at least a portion of the cannula and stylet into the patient subcutaneously; routing the cannula and stylet to a location proximate to an occipital area of the patient's skull; optionally removing the stylet from the cannula; inserting a guidewire through the hollow passage of the cannula, and/or optionally through the stylet; steering the guidewire around the occipital area and to a second incision located proximate the patient's skull, wherein said steering is achieved without the use of a third incision; attaching the tubing to the guidewire through the second incision; and retracting the guidewire, attached tubing, and/or stylet via the first incision.

A tunneling guidewire system is also disclosed herein for subcutaneously routing tubing within a human patient. The system may include, for example, a cannula having hollow passage; and a guidewire configured to extend through the hollow passage of the cannula; wherein the guidewire comprises a stiffness, k, between about 100,000 and 30,000,000 newtons per meter.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which.

DETAILED DESCRIPTION

Figure 1:
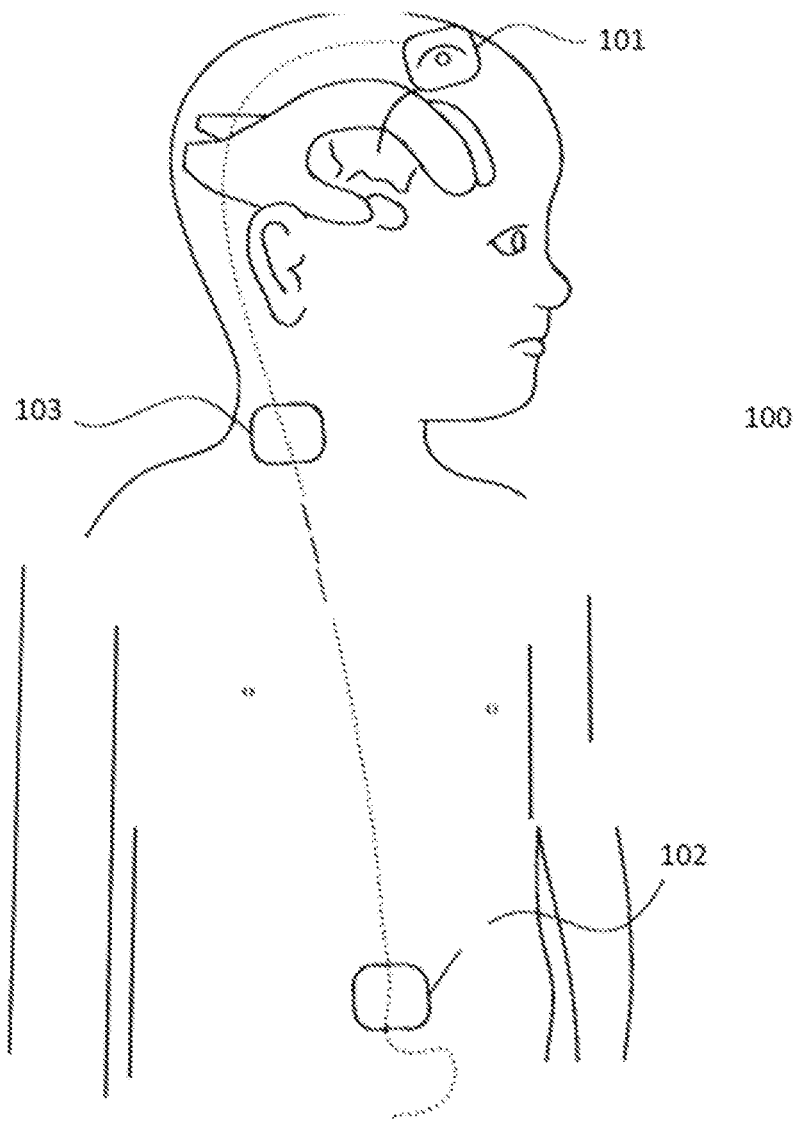
FIG. 1 is a schematic illustration of incision locations performed in a traditional hydrocephalus ventriculoperitoneal shunting system installation procedure.

Reference will now be made to various example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The described progression of processing operations described are merely examples, however, and the sequence of operations is not limited to that set forth herein and may be changed as is known in the art, with the exception of operations necessarily occurring in a certain order. Also, description of well-known functions and constructions may be omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Various example embodiments of the present general inventive concept, as described herein, provide a medical device insertion tool/system, and a method of using the system, to implant surgical drainage tubing during the installation of a ventriculoperitoneal hydrocephalus shunt, or the like, with surgical instruments inserted into a patient from a single proximal entry point to avoid excessive incisions made to the patient. Instruments such as this tool/system may be comprised of a cannula, a blunt nose stylet, and a guidewire or guidewire stylet.

Throughout this disclosure reference is made to a guidewire and/or guidewire stylet. For the purposes of this disclosure, the terms "guidewire" and "guidewire stylet" are interchangeable and used broadly to cover any and all embodiments comprising a guidewire and/or a guidewire stylet. For example, a "guidewire" comprises a "guidewire stylet" and, similarly, a "guidewire stylet" comprises a "guidewire." In instances where one term in particular is being discussed, that fact is identified with particularity. The interchanging use of these terms is not intended to limit this application in any way.

The guidewire may have a loop endpoint offering rounded edges, in which such tool/system may be overall utilized for the subcutaneous guidance or manipulation for attaching surgical tubing, after the subcutaneously routing to form a continuous path from the first incision to the second incision. Once this subcutaneous path is established the surgical shunt tubing is attached to the loop endpoint of the guidewire and then the subcutaneously routed tools are removed either as to include all parts or removing the parts separately to subcutaneous route the tubing without the need for the third incision.

All the instruments are hand or machine malleable, with rounded non-bur edges so as to not unacceptably tear patient tissue during the procedure. Furthermore, the guidewire can be constructed of any number of hardened material(s) or steel alloys such as hardened materials and alloys of high carbon steel, or stainless steel alloy, or such as spring hardened stainless steel, including for example, piano wire or any of the stainless steel alloys of types 17-4 or 17-7, which are herein considered smart materials, including those materials, traditionally known to one skilled in the art, as smart materials whose material properties are changed by a physical stimulus such as, but not limited to, Nitinol™. The purpose of this smart material is to first offer a fixed manipulatable shape for the guidewire into a custom rounded form and then, secondly, to insert it into an approximately straight cannula of small diameter for which the guidewire will rebound to its original manipulated shape that was ultimately custom arranged for the patient's routing path.

The guidewire material may be a strategically designed alloy manufactured to produce a hardened and tempered finish for an elastic, yet malleable, component with the proper balance of mechanical properties, including a sufficiently high yield strength and an appropriate modulus of elasticity for the intended use, so as to produce a shape memory smart material component for programming via manual manipulation, or shaping, which will thereafter endure the straightening stresses associated with the shape memory component, or smart material, traversing the cannula's interior, which will once again return to its approximate programmed shape upon exiting the cannula with sufficient stiffness. This preformed shape, made by a surgeon, must approximately retain this shape after passing through a cannula and return to its performed shape, determined by a surgeon, without excess bend return error, and thus is a requirement for the smart material to rebound to a preformed custom patient dependent curvilinear shape. This pre-shaping can be aligned with the instrument's handle, which may be optionally offset, or other such indicator or marker, to orient the guidewire stylet and its loop from a proximal operator position. The guidewire stylet should possess sufficient stiffness in order to be able to penetrate and traverse subcutaneous tissue and be guided proximally by the operator. The stiffness of the material, defined by k, with units of force per unit length, can be determined from:

$$k = \frac{A \cdot E}{l}$$

where, A is the guidewire material's cross-sectional area, E is the material's Young's Modulus (i.e. its Modulus of Elasticity), and l is the guidewire's length.

In example embodiments described herein, the medical device insertion tool/system represents a cannula, a blunt nose stylet to aid in the subcutaneous tunneling process, and a guidewire stylet instrument of the present general inventive concept. However, it is understood that the instruments, which may be utilized in the systems and methods of the present general inventive concept, are not limited to trocars, tunnelers, introducers, or stylet(s), for tunneling or other general medical procedures. Also, in various example embodiments the terms "single entry" is used to indicate the beginning of a subcutaneous routing path for the instruments, which begins at an incision location and then is routed inside a patient's body, which may not be viewable by the naked eye, but may alternatively be viewed by skin moving as the subcutaneous routing progresses along the routing path.

Various example embodiments of the present general inventive concept provide a single entry subcutaneous tunneling trocar system. Example embodiments of the present general inventive concept are given below.

Such advantages as described herein, as well as other advantages not explicitly stated herein, overcome many of the previously described limitations of a conventional hydrocephalus shunt installation surgical procedure by providing a novel proximal, or other entry 101 or 102 that is optionally single entry, surgical subcutaneous routing of surgical tubing with the described cannula, stylet, and guidewire, which then allows for the continuous subcutaneous tunneling of drainage tubing, eliminating the typical intermediate incision normally located at 103.

In one example embodiment, the guidewire is a guidewire stylet. In that embodiment, the guidewire stylet may be used to replace the stylet within the cannula prior to steering the guidewire to the desired location. In another example embodiment, the guidewire may be used in conjunction with the stylet. For example, the stylet may have a hollow passage through which the guidewire may be inserted.

Figure 2A:
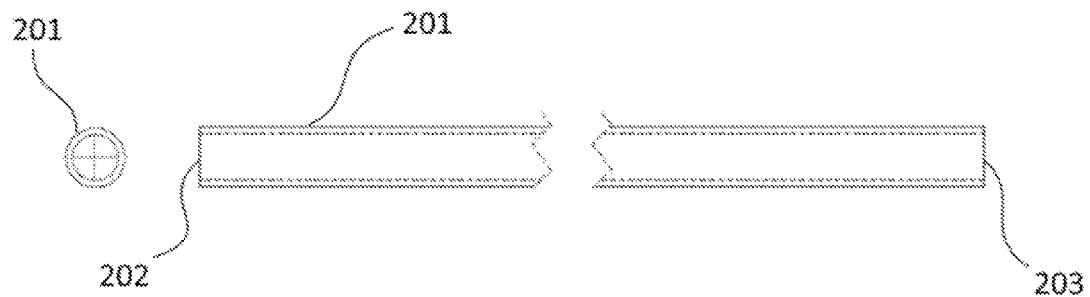
FIG. 2A is a schematic of an example cannula.
Figure 2B:
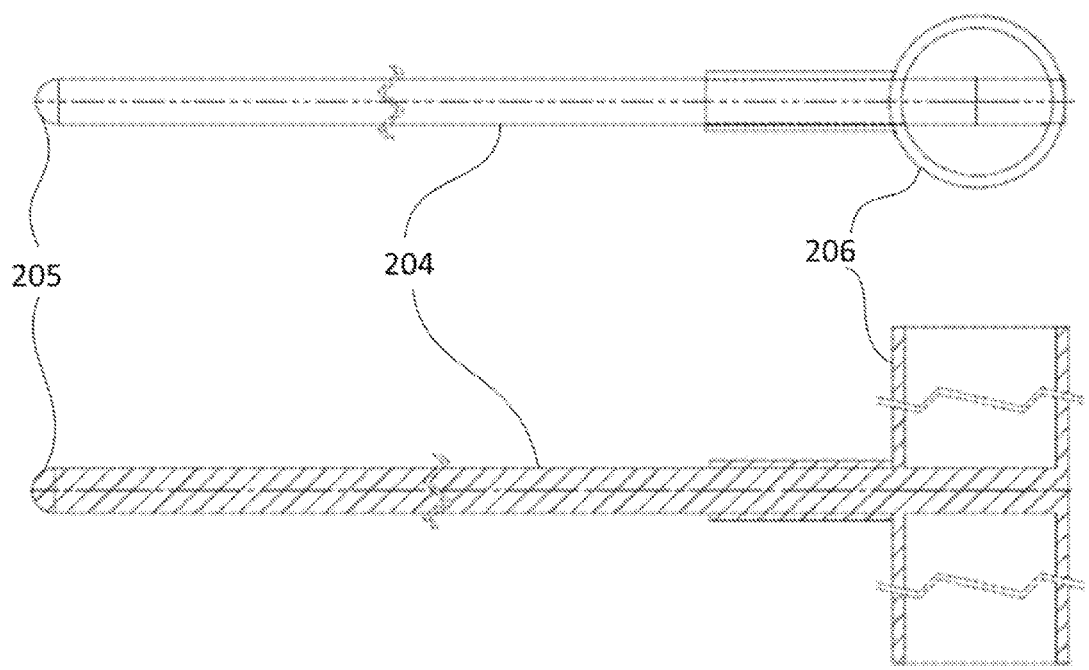
FIG. 2B is a schematic of an example stylet
Figure 2C:
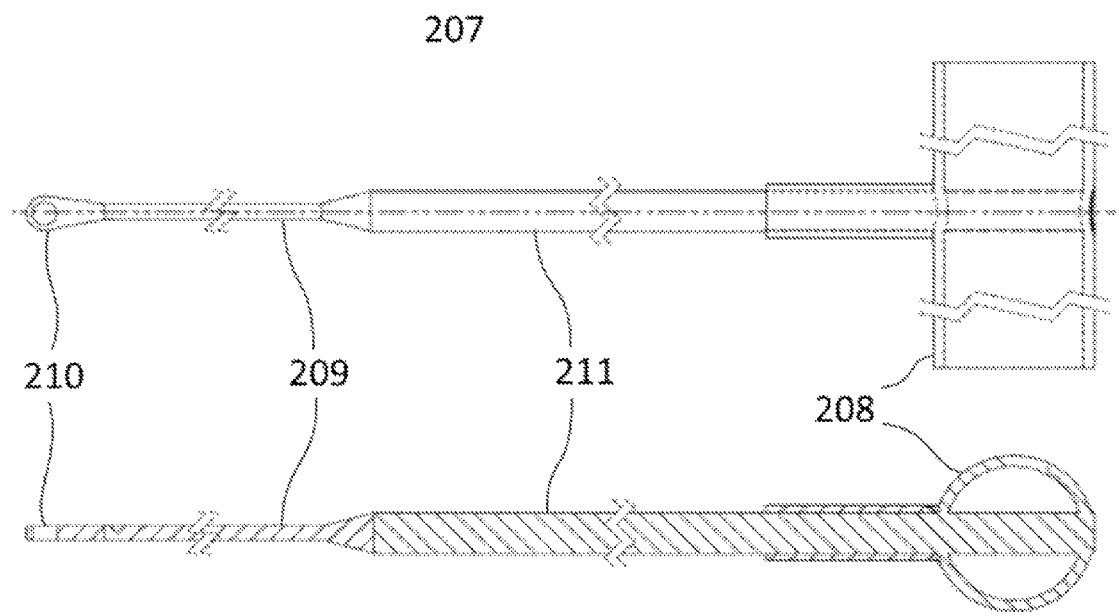
FIG. 2C is a schematic of an example guidewire stylet having an endpoint loop.

FIGS. 2A-2C are schematic illustrations of a trocar system, having a at least one cannula 201, at least one stylet 204, and at least one guidewire stylet 207 including at least one eyelet 210 or attachable endpoint, which resists subcutaneous skin puncture, but results in an advantageous subcutaneous protuberance visible along a routed path, which allows for a surgeon to visualize and further optionally hand steer the guidewire stylet, 207, during the subcutaneous routing process. It is noted that although a trocar is described in the example embodiment of FIGS. 2A-2C, various other multi-instrument trocars may be used according to other various example embodiments of the present general inventive concept without deviation from the basic teaching for subcutaneously routing the tubing.

The multi-instrument trocar illustrated in FIGS. 2A-2C includes a first semi-rigid trocar or cannula 201 having a first end 202 and a second end 203, which can contain the stylet 204 inserted with an optional bullet nose 205 end first into the first end point 202 of cannula 201, which can then be subcutaneously tunneled from a second incision 102 to an approximate location where the conventional incision 103 would have been located by utilizing the leverage created by stylet handle 206. Optionally the handle 206 can have a stylet collar that extends beyond a surgeons fingers, or other protection guards attached to the cannula or stylet and/or other protective grips such as ring grips on the stylet, to prevent the surgeon from pinching or injuring the user's gloves, skin, and/or fingers when fully inserting the stylet 204 or guidewire stylet 207 into the cannula. These examples are simply given as examples to protect a surgeon's hands/fingers during the procedure but are not limited to these examples. The location 103 is generally located around the patient's retro-auricular occipital area, or approximately around the patient's nuchal line. Generally, the cannula 201 and stylet 204 may be slightly bent to aid in the subcutaneous routing within a patient. Handles 206 and 208 are added for obtaining maximum leverage and maneuverability for the surgeon to manipulate and guide the instrument 200 during patient in-vivo subcutaneous routing.

Once the instrument containing both the cannula 201 and stylet 204 reaches the subcutaneous endpoint approximately around the ear and/or nuchal line the stylet 204 is removed and replaced with a preformed guidewire stylet 207. The guidewire stylet 207 may optionally be constructed with varying sizes of diameters, while no element is necessarily required to be made of the same material as the remainder of the other components, and whereby handle 208 may optionally be offset such that it can be parallel with a preformed bend and loop 210 in the guidewire portion 209 to indicate its position while subcutaneous, in which such guidewire portion 209 and loop 210 may be routed through and beyond the cannula, and in which guidewire portion 209 returns to its performed shaped due to its smart material after it passes through (i.e. when guidewire portion 209 exits) cannula 201. The guidewire portion 209 may then be guided to traverse a patient's nuchal line with penetration endpoint 210, which is curved/rounded so as to facilitate such traversal. Once the guidewire portion 209 and looped endpoint 210 passes the nuchal line and enters the subcutaneous region under the scalp it tends to return to its curvilinear preformed shape as it exits the cannula 201 and easily tunnels while being optionally hand guided subcutaneously to the desired area. The guidewire stylet is steerable subcutaneously by a surgeon's hand to aid in the guidance of the routing if needed. It is noted that stylet portion 211 and guidewire portion 209 are attached as one unit during the procedure. Once the guidewire stylet passes completely through the first incision 101, the surgical tubing is securely attached to the endpoint 210 by tying a knot, glue, suture, staple, screw, clamp, or any other mechanical or electromechanical attachment means to securely attach the tube to the endpoint 210, and therefore to the entire assembly residing inside cannula 201, which is then removed by either pulling the guidewire stylet 207 or the entire assembly back through the subcutaneously routed tunnel path leaving behind the subcutaneously routed shunt tubing without the need for the third incision typically required for such routing normally located around a patient's neck. It is noted that the interface between elements 211 and 209 are smooth and without burrs or rough edges similar to the other components edges, which are substantially free from burrs or rough edges.

In another embodiment the end point loop 210 can optionally be separately attached with replacement elements like 210, or other useful attachments, which can be secured to element 209. The same replacement logic applies to the connection between elements 211 and 209 and can be optionally separately replaced with different useful attachments. It may also be useful to construct all the elements in the trocar system, cannula 201, stylet 204, and guidewire stylet 207, to be optionally made of 100% stainless steel components, without presenting any burrs or rough edges, which may induce undue tissue snagging during routing.

Figure 3:
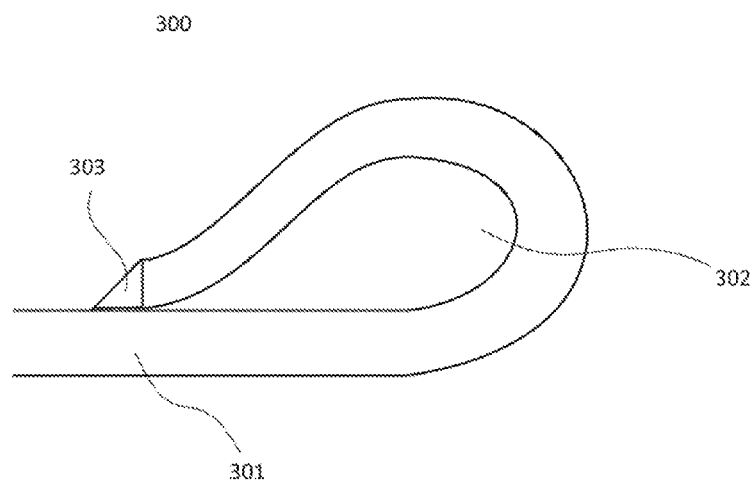
FIG. 3 is a schematic of an example endpoint loop.

The design of the end-point 210 is decisively important, because it has the dual purpose of traversing subcutaneous tissue and the occipital bone's nuchal lines while offering attachment of surgical tubing for retraction back through the subcutaneously tunneled path. It must also easily pass through the cannula without excessive drag or becoming stuck. The end-point 210 is further described by the embodiment shown in FIG. 3. The loop, generally indicated by 300, may optionally be constructed from the same wire material and diameter as that of guidewire portion 209. The diameter of the loop, 302, is preferred to be large enough so as to easily allow attachment of shunt tubing, by various methods previously described, while still yet allowing the loop 300 to be small enough to easily pass through cannula 201. The hole 302 may optionally be a drilled hole. The loop formed, as shown in FIG. 3, may optionally be closed by permanent weld, brazing, or other mechanical/electromechanical means to form connection point 303. However, the loop, or hole, may optionally be closed or attached by an inter-changeable screw, for instance to allow for interchangeable endpoints. Furthermore, the loop's outermost apex may optionally include intentional serrations for efficiently traversing subcutaneous tissue and in forming a subcutaneous pathway. Additionally, the guidewire end point 300 can be optionally separately attached to the stylet 207 so as to allow for increased operating range of the tool, with respect to cannula or tubing size, as the guidewire stylet 207 being optionally separately attachable to the element 205 to allow different use cases or allowing the user to use disposable guidewire stylet 207. The handles 206 and 208 could also be interchangeable with other handles or tools in order to make the surgery more efficient. As yet another example, the preformed bend of the guidewire portion 209 and the guidewire stylet's endpoint 300 could be constructed or bent to further align with the orientation of the main preformed bend or handle 206 and 208 to help visually indicate and guide guidewire stylet 207 during subcutaneous routing. A further example of this application would be the incorporation of sensors or location indicators into the cannula 201 or guidewire stylet 207 to further monitor and position ally indicate the routing during installation of the procedure and further install sensors to monitor shunt tubing characteristics over time such as movement, etc. The sensors could also be minimized and made compatible with existing medical imaging equipment. Additionally, the need to reposition the endpoint after subcutaneously routing can be optionally completed by inserting a second smaller cannula into cannula 201 then insert the guidewire stylet 207 through the second cannula after repositioning. Optionally, the cannula can have an interface such as threads or other attachment to the second cannula or guidewire stylet 207.

Figure 4:
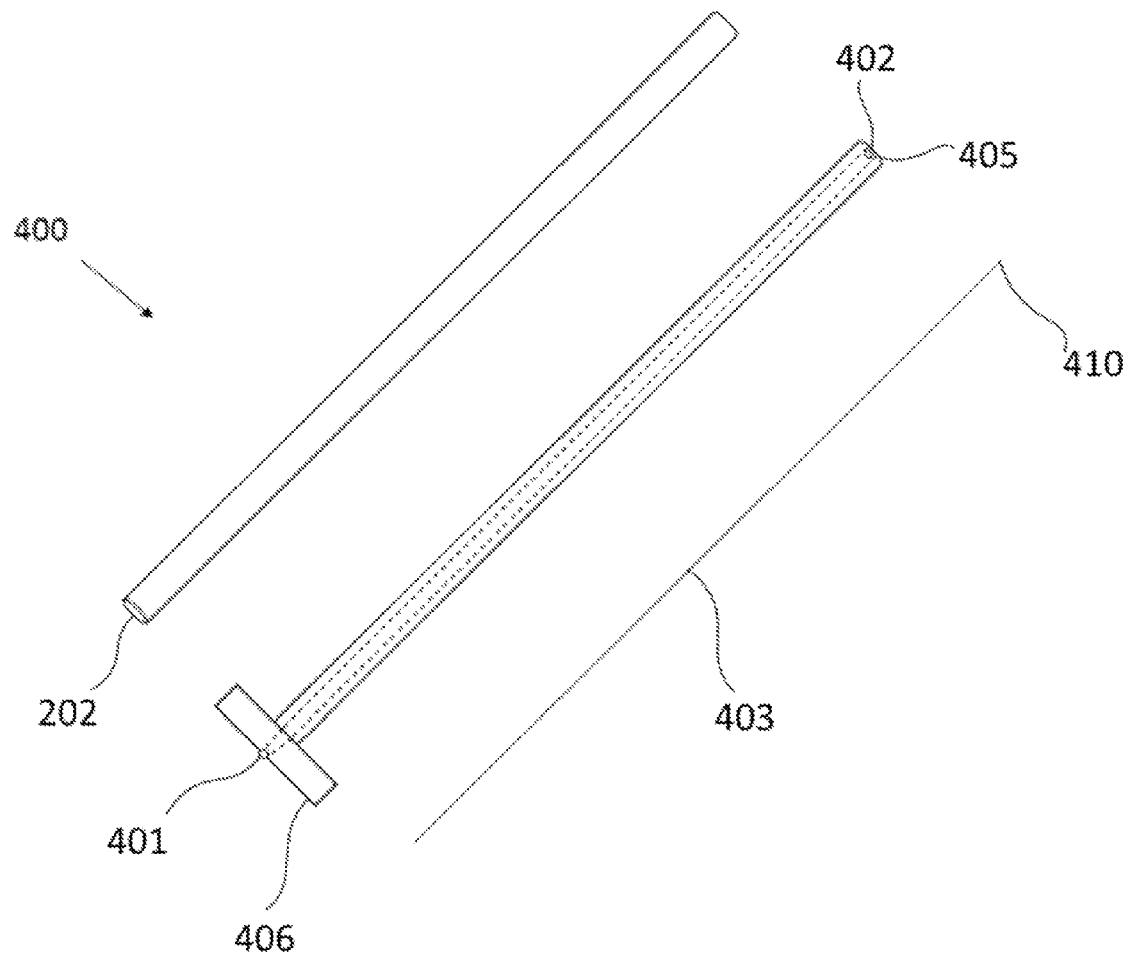
FIG. 4 is a schematic of an example cannula, stylet, and guidewire.

FIG. 4 is a schematic illustration of a trocar system, generally indicated by 400, having at least one cannula 201, at least one stylet 404, and at least one guidewire stylet 403 with an endpoint 410. It is noted that although a trocar or tunneler is described in the example embodiment of FIG. 4, various other multi-instrument trocars or tunnelers may be used according to other various example embodiments of the present general inventive concept without deviation from the basic teaching for subcutaneously routing the tubing or other such device.

The multi-instrument trocar illustrated in FIG. 4 includes a first semi-rigid trocar or cannula 201 having a first end 202 and a second end 203, which can contain the stylet 404 inserted, with an optional bullet nose 405 end, first into the first end point 202 of cannula 201, which can then be subcutaneously tunneled from a second incision 102 to an approximate location where the conventional incision 103 would have been located by utilizing the leverage created by stylet handle 406. The location 103 is generally located around the patient's occipital area near the ear or approximately around the patient's nuchal line. Generally, the cannula 201 and stylet 404 may be slightly bent to aid in the subcutaneous routing within a patient. Handle 406 are added for obtaining maximum leverage and maneuverability for the surgeon to manipulate and guide the instrument 404 during patient in-vivo subcutaneous routing. Optionally the handle 406 can have a stylet collar that extends beyond a surgeons fingers, or other protection guards, attached to the cannula or stylet and/or other protective grips such as ring grips on the stylet, to prevent the surgeon from pinching or injuring the user's gloves, skin, and/or fingers when fully inserting the stylet 404 into cannula 201 or a manipulatable guidewire stylet 403 into stylet's 404 hollow passage 401 until the guidewire stylet endpoint 410 extends beyond the endpoint of the stylet's endpoint 405 via the hollow passage endpoint 402. For clarity, it is additionally noted that stylet 404 contains an open hollow tubular passage, with endpoints 401 and 402, that extends completely through the stylet 404, including any added length by handle 406, for allowing the guidewire stylet 403 to pass through the stylet 404.

Once the instrument containing both the cannula 201 and stylet 404 reaches the subcutaneous endpoint approximately around the patient's occipital area near the ear and/or nuchal line, the stylet 404 is not removed, but left in place in-vivo while guide wire stylet 403 is inserted completely through stylet 404 until the stylet's end point 410 extends beyond the end of the stylet 404 denoted by 405. The guidewire stylet is steerable subcutaneously by a surgeon's hand to aid in the guidance of the routing if needed. Once the guidewire stylet passes completely through the first incision 101, the surgical tubing is securely attached to the endpoint 410 by tying a knot, glue, suture, staple, screw, clamp, pressure fitting, or any other mechanical or electromechanical attachment means to securely attach the tube to the endpoint 410, and therefore to the entire assembly 404 residing inside cannula 201, and is then removed by either pulling the guidewire stylet 403 out or the entire assembly consisting of guidewire stylet 403, stylet 404, and optionally cannula 201, back through the subcutaneously routed tunneled path leaving behind the subcutaneously routed shunt tubing without the need for the third incision typically required for such routing normally located around a patient's neck. It is noted that the interface between elements 403 and 404 are smooth and without burrs or rough edges similar to the other components edges, which are substantially free from burrs or rough edges. Stylet 404 must also easily pass through the cannula without excessive drag or becoming stuck. The stylet 404 could also be used to help clear an obstruction blocking the tunneling path and therefore allow the use of the previously disclosed methods and embodiments.

We claim:

1. A tunneling guidewire system for subcutaneously routing tubing within a human patient, comprising:
    a cannula defining a hollow passage; and
    a guidewire extendable through the hollow passage of the cannula;
    wherein the guidewire comprises a stiffness, k, between about 100,000 and 30,000,000 Newtons per meter for extravascularly routing the guidewire.

2. The tunneling guidewire system of claim 1, wherein the guidewire comprises a proximal end and a distal end, the proximal end being coupled to a stylet, the stylet and the guidewire being removably disposable within the hollow passage of the cannula.

3. The tunneling guidewire system of claim 2, wherein the guidewire is permanently affixed to the stylet.

4. The tunneling guidewire of claim 2, wherein at least a portion of the stylet has a first outer diameter and at least a portion of the guidewire has a second outer diameter that is less than the first outer diameter.

5. The tunneling guidewire system of claim 2, wherein the cannula, guidewire, and stylet consist of stainless steel.

6. The tunneling guidewire system of claim 1, wherein the guidewire comprises a tip comprising an endpoint loop.

7. The tunneling guidewire system of claim 1, wherein the cannula comprises a first end, a second end, a first portion associated with the first end, and a second portion associated with the second end, wherein the second portion comprises a bend such that the second end is located at a point between 0 degrees and 45 degrees from an axis aligned with the first portion.

8. The tunneling guidewire system of claim 1, wherein the guidewire comprises a handle adjacent a proximal end of the guidewire, wherein the guidewire is steerable via the handle.

9. The tunneling guidewire of claim 8, wherein the cannula comprises a proximal end and a distal end, and the guidewire handle has an outer perimeter that is larger than an inner diameter of the proximal end of the cannula, wherein the guidewire handle cannot pass through the proximal end of the cannula.

10. The tunneling guidewire of claim 9, wherein the guidewire handle is a T-shaped handle.

11. The tunneling guidewire system of claim 1, wherein the guidewire is pre-bent such that a portion of the guidewire comprises a minimum bend radius of about one centimeter.

12. The tunneling guidewire system of claim 11, wherein the portion of the guidewire that is pre-bent is pre-bent to substantially match the parietal bone radius of a patient's skull.

13. The tunneling guidewire system of claim 1, wherein the guidewire comprises a tensile strength range from about 300 mega-pascals to about 3,500 mega-pascals.

14. The tunneling guidewire system of claim 1, wherein the guidewire comprises a Young's modulus of at least 30 giga-pascals, but not more than about 400 giga-pascals.

15. The tunneling guidewire system of claim 1, wherein the guidewire comprises a tip defining an eyelet.

16. The tunneling guidewire system of claim 1, wherein a distal end of the guidewire comprises a tip, the tip comprising a proximal end, a distal end, and an intermediate portion between the proximal end and the distal end, wherein an outer perimeter of the intermediate portion is greater than an outer perimeter of the proximal end and an outer perimeter of the distal end.

17. The tunneling guidewire system of claim 1, wherein the cannula and guidewire comprise stainless steel.

18. A tunneling guidewire system for subcutaneously routing tubing within a patient, the system comprising:
   a cannula defining hollow passage; and
   a guidewire-stylet comprising a guidewire portion and a stylet portion, the guidewire portion being coupled to the stylet portion, the guidewire-stylet being extendable through the hollow passage of the cannula, wherein the guidewire portion comprises a stiffness, k, between about 100,000 and 30,000,000 Newtons per meter for extravascularly routing the guidewire portion.

19. The tunneling guidewire system of claim 18, wherein at least a portion of the guidewire portion is pre-bent to substantially match the parietal bone radius of a patient's skull, and wherein the pre-bent portion of the guidewire portion is straightened when disposed within the cannula and bent when disposed outside of the cannula.

20. The tunneling guidewire system of claim 19, wherein the pre-bent portion of the guidewire portion comprises a tip, the tip defining an opening for receiving a drainage tube.

21. The tunneling guidewire system of claim 18, wherein the stylet portion comprises a proximal end and a distal end, and the guidewire portion extends from the distal end of the stylet portion, and a handle is coupled to the proximal end of the stylet portion, the handle having an outer perimeter that is greater than an inner diameter of the cannula such that the handle cannot pass through the cannula.

* * * * *